United States Patent
Benes et al.

(10) Patent No.: US 6,690,015 B1
(45) Date of Patent: Feb. 10, 2004

(54) METHOD FOR THE SPECTROSCOPIC DETERMINATION OF THE CONCENTRATION OF ALCOHOLS WITH 1 TO 5 CARBON ATOMS

(76) Inventors: Roman Benes, Kasernstrasse 82, Graz (AT), A-8041; Josef Pleschiutschnig, Bahnhofstrasse 1, Bleiburg (AT), A-9150; Franz Reininger, Trattengasse 38c, Villach (AT), A-9500; Alessandro Del Bianco, Trattengasse 38b, Villach (AT), A-9500

( * ) Notice: Subject to any disclaimer, the term of this patent is extended or adjusted under 35 U.S.C. 154(b) by 0 days.

(21) Appl. No.: 09/673,906

(22) PCT Filed: Feb. 24, 2000

(86) PCT No.: PCT/AT00/00050

§ 371 (c)(1),
(2), (4) Date: Dec. 27, 2000

(87) PCT Pub. No.: WO00/50893

PCT Pub. Date: Aug. 31, 2000

(30) Foreign Application Priority Data

Feb. 25, 1999 (AT) ................................................ 323/99

(51) Int. Cl.[7] .......................... G01N 21/35; G01N 33/14
(52) U.S. Cl. .............. 250/339.12; 250/343; 250/339.09
(58) Field of Search ....................... 250/339.03, 339.09, 250/339.11, 339.12, 343

(56) References Cited

U.S. PATENT DOCUMENTS

| | | | | |
|---|---|---|---|---|
| 4,228,192 A | * | 10/1980 | Sanden | 250/339.11 |
| 5,126,570 A | * | 6/1992 | Boos | 250/339.11 |
| 5,227,986 A | * | 7/1993 | Yokota et al. | 123/1 A |
| 5,239,180 A | * | 8/1993 | Clarke | 250/339.07 |
| 5,262,645 A | * | 11/1993 | Lambert et al. | 250/339.11 |
| 5,362,965 A | * | 11/1994 | Maggard | 250/339.04 |
| 5,679,955 A | * | 10/1997 | Schmidt et al. | 250/339.12 |
| 5,747,806 A | * | 5/1998 | Khalil et al. | 250/339.09 |
| 5,750,995 A | * | 5/1998 | Clarke | 250/339.09 |
| 5,763,883 A | * | 6/1998 | Descales et al. | 250/339.09 |
| 6,043,504 A | * | 3/2000 | Fujita et al. | 250/339.12 |

FOREIGN PATENT DOCUMENTS

WO    WO 9317324 A1 * 9/1993 ........... G01N/21/35

OTHER PUBLICATIONS

Buchanan et al., "Detection of Ethanol in Wines Using Optical Fiber Measurements and Near–Infrared Analysis", Applied Spectroscopy, vol. 42, No. 6 (1998), pp. 1106–1111.*

Cavinato et al. "Noninvasive Method for Monitoring Ethanol in Fermentation Processes Using Fiber–Optic Near Infrared Spectroscopy", Analytical Chemistry, vol. 62, No. 18 (Sep. 1990), pp. 1977–1882.*

* cited by examiner

Primary Examiner—Albert Gagliardi
(74) Attorney, Agent, or Firm—Townsend and Townsend and Crew, LLP

(57) ABSTRACT

A method for spectroscopically determining the concentration of alcohols with 1 to 5 carbon atoms, especially ethanol, in liquid probes, especially alcohol-containing food products, healing preparations, cosmetic products and the like. The absorption of light by the probe is measured at at least one wave length in the range of 1100 nm to 1300 nm, and preferably in the range of 1150 nm to 1250 nm. The alcohol concentration is determined from the measured absorption with the help of a calibration. The alcohol content of a liquid probe can be determined in a simple and fast manner and over a large concentration range.

11 Claims, 3 Drawing Sheets

METHOD FOR THE SPECTROSCOPIC DETERMINATION OF THE CONCENTRATION OF ALCOHOLS WITH 1 TO 5 CARBON ATOMS

BACKGROUND OF THE INVENTION

The present invention concerns a method for spectroscopically determining the concentration of alcohols having 1 to 5 carbon atoms, especially ethanol, in liquid probes such as alcohol-containing food products, healing preparations, cosmetic products and the like.

The spectroscopic determination of low alcohol concentrations, particularly ethanol, in liquid probes is widespread. With so-called near-infrared-spectroscopy (NIR), it is possible to qualitatively and/or quantitatively determine a variety of parameters. NIR-spectroscopy typically takes place in a wave length range of between about 700 nm to about 2500 nm. Superimposed or combination oscillations, rather than base oscillations, are normally measured. In this wave length range, however, the absorption capacities of the substances under investigation are relatively low, and the absorption bands are wider and frequently overlap or are superimposed. This complicates the interpretation of the measurements and can even prevent one from obtaining unambiguous and reproducible measurements. Yet, the increasing demand and opportunities for spectroscopic analysis in this wave length range and the availability of inexpensive components, such as fiberoptics, semiconductor detectors and new light sources, create a need for the fast and quick analysis of probes by means of NIR-spectroscopy with the help of simple instruments.

U.S. Pat. No. 5,679,955, for example, discloses a method of the above-named type for spectroscopically determining the concentration of low alcohols, particularly ethanol, in liquid probes. Transmission measurements in the infrared region are taken at a single wave length. This known method operates in a wave length range which is selected so that the absorption from the water contained in the probe exceeds the absorption of the additionally contained alcohol, while taking into consideration that the predominant part of such an alcohol-containing probe is formed by ethanol and water. Multiple calibration measurements are taken, each at a given wave length. The alcohol content of additional probes is determined on the basis of the previously established calibration parameters. According to this known state of the art, it is proposed to conduct the measurements at wave lengths of about 0.98 $\mu$m, about 1.3 $\mu$m, and about 1.45 $\mu$m, to take into account the absorption coefficients for water and ethanol. A disadvantage of this prior art method is the fact that measurements must be taken at wave lengths where the absorption coefficient of water is above that for ethanol. As a result, the determination of the alcohol content has a high degree of inaccuracy, and according to U.S. Pat. No. 5,679,955 is limited to determining alcohol contents of less than 10% (volume). Thus, the known method is essentially limited to determining the alcohol concentration of beers. Beverage and general liquid probes having higher alcohol contents, such as wines, brandies, healing preparations, as well as cosmetic products, cannot be analyzed with this method. In addition, the known methods do not readily lend themselves to taking into consideration the presence of other substances, which can significantly affect the measurements.

SUMMARY OF THE INVENTION

It is an object of the present invention to provide a method for spectroscopically determining the concentration of alcohols having 1 to 5 carbon atoms, especially ethanol, in liquid probes, which permits the determination of alcohol contents, particularly ethanol concentrations, in liquid probes over a wide concentration range and with greater accuracy. This is accomplished in accordance with the present invention with a method of the above-mentioned type which is essentially characterized in that the light absorption of the probe under investigation is analyzed at at least one wave length in the range from 1100 nm to 1300 nm, and preferably in the range from 1150 nm to 1250 nm. The alcohol concentration is determined from the measured absorption with the aid of a calibration. By measuring, in accordance with the present invention, the light absorption of the probe being investigated at at least one wave length in the range from 1100 nm to 1300 nm and preferably in the range of 1150 nm to 1250 nm, the measurement takes place in a wave length range in which the absorption spectrum of the alcohol that is to be measured, particularly ethanol, has a pronounced absorption maximum. This makes it possible to readily separate and distinguish it from the absorption spectrum of water which constitutes the predominant part of such a probe. In accordance with the invention, the alcohol content of the probe under investigation is then directly determined from the measured absorption in the stated wave length range. The determination of the alcohol content makes use of a previously established calibration based on either an artificial probe, for example a water-alcohol mixture, or a real probe, for example beer, wine or the like.

In accordance with an especially preferred embodiment of the invention, it is proposed to measure the absorption in the range from 1170 nm to 1200 nm. The reason for this is that in this wave length range the absorption coefficient of ethanol has a pronounced maximum, while the absorption coefficient of water is not only essentially constant, but also lower than the absorption coefficient of ethanol. It is further preferred to take the absorption measurements in wave length ranges in which the absorption coefficient of water contained in the probe is essentially linear and preferably constant as well. This makes it possible to consider in a simple manner what part of the total measured absorption is caused by the water contained in the probe.

As already briefly mentioned above, in addition to the main constituents of the probe under investigation, low alcohol, especially ethanol, and water, other substances can at times be present which may influence the determination of the ethanol concentration in the probe being investigated. In addition to the above-discussed selection criteria of the present invention for selecting the wave length range, the present invention further proposes to preferably conduct the absorption measurement in a wave length range in which the absorption characteristics of the other substances in the probe are essentially linear. This makes it possible to take into consideration what part of the measured absorption was contributed by the other substances when determining the concentration. In this context, it is particularly preferred that the wave length is selected so that the absorption proportions contributed by the other substances essentially cancel each other at the selected wave length, or at which they can be taken into consideration in a simple manner by using corresponding, predetermined calibration constants.

To enhance the accuracy with which the alcohol concentration is determined, it is further proposed to measure the light absorption at at least two wave lengths, and preferably three wave lengths. By using at least two and preferably three wave lengths, several absorption values of the probe under investigation can be quickly determined. Simple evaluation methods make it possible to adapt and exploit the measured values and then compare them with the previously determined reference values of at least one calibration measurement. For a simple evaluation of the light absorption values of the probe under investigation at several wave lengths, the present invention proposes to preferably determine the alcohol concentration for the absorption values at the different wave lengths with a linear approximation method, for example a linear regression, a multilinear regression, or the like. Comparing the absorption values with the reference values from the calibration measurement with the help of such simple approximation methods provides adequate results without having to resort to burdensome evaluation and calculation methods.

By taking into consideration that the spectroscopic determination of alcohol concentrations at at least one wave length in a range in which the absorption coefficient of ethanol has a pronounced maximum, while the absorption coefficient of water and of other substances that may be present is essentially linear and preferably constant, the present invention makes it possible to determine the alcohol concentration in the probe under investigation over a very much larger concentration range and with corresponding accuracy. In this context, the present invention particularly prefers to use probes having ethanol concentrations of less than 60%.

To further enhance the accuracy with which the alcohol concentration is determined, it is proposed to measure the absorption at a constant probe temperature. Alternatively, or additionally, and in accordance with a further preferred embodiment of the inventive method, the temperature of the probe being analyzed is taken into consideration. Such a constant temperature or temperature stabilization of the probe makes the determination of the ethanol concentration more accurate, or the temperature dependence of particular parameters can be taken into consideration with reference to the actual probe temperature. It is further preferred that the temperature of the probe is determined with an accuracy of $\pm 0.5°$ C., especially $\pm 0.2°$ C. This helps attain the desired accuracy of $\pm 0.2\%$ by volume, and especially $\pm 0.1\%$ by volume with which the ethanol concentration is determined.

BRIEF DESCRIPTION OF THE DRAWINGS

In the following, the invention is described in more detail with reference to the drawings, which show an example for performing the method of the present invention. The drawings show.

DESCRIPTION OF THE PREFERRED EMBODIMENTS

Figure 1:
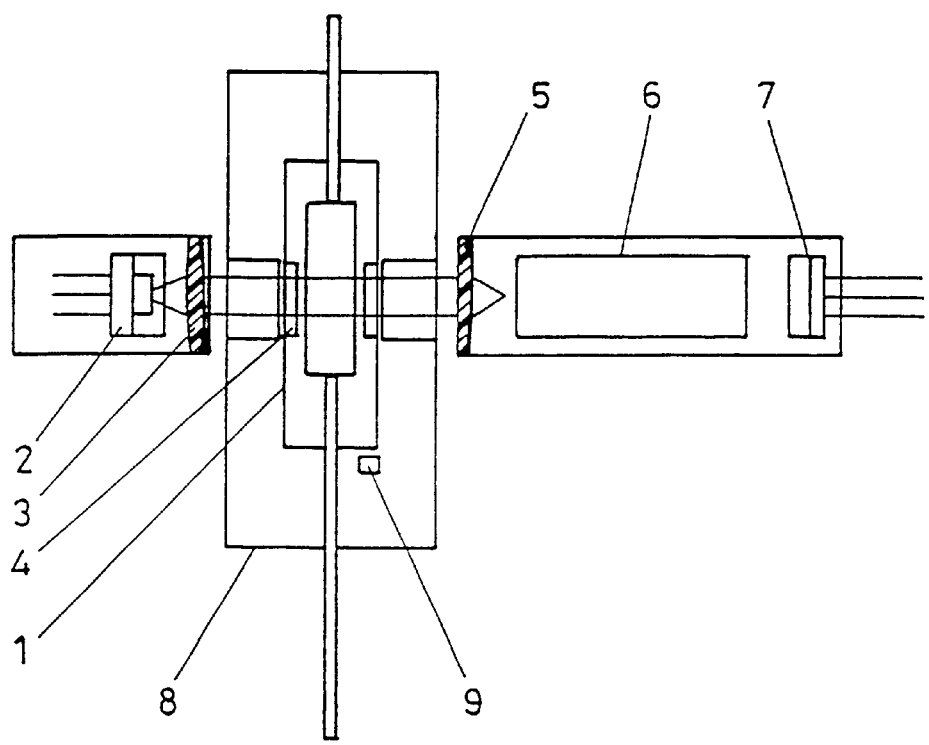
FIG. 1 schematically illustrates a system for performing the method of the present invention.
Figure 2:
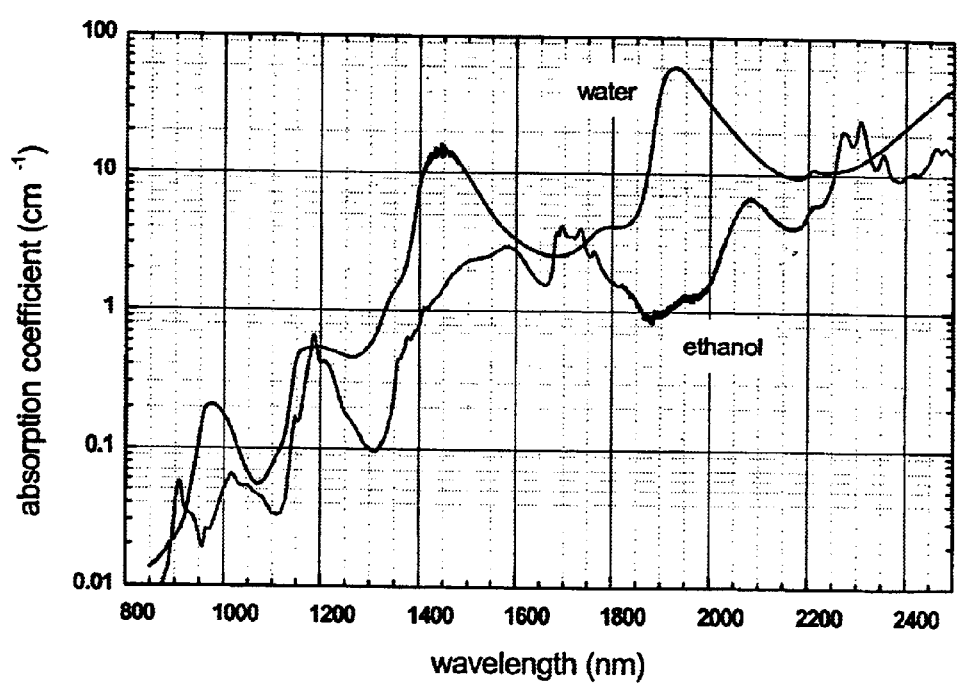
FIG. 2 shows the absorption spectra of water and ethanol for the range of NIR spectroscopy.
Figure 3:
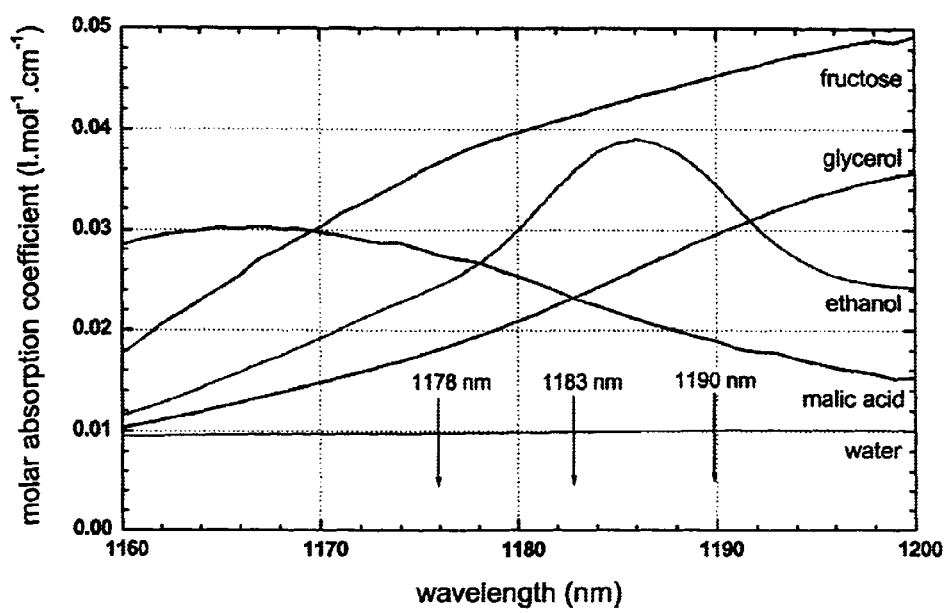
FIG. 3 shows the absorption spectra over a limited absorption range for water and ethanol as well as other substances that may be present, for example in wine.

FIG. 1 shows an arrangement for performing a method for spectroscopically determining the concentration of low alcohols in liquid probes. A probe under investigation is in a cuvette 1, and a light source 2, for example a diode in the infrared range, is used. Electromagnetic radiation in a selected wave length range reaches cuvette 1 via schematically shown optics 3 and a glass window 4. The radiation further passes through appropriate optics 5 and a dispersion element 6 to a detector 7 such as, for example, a semiconductor array. FIG. 1 further shows an enclosure 8 for thermally stabilizing the probe being analyzed and a sensor 9 for measuring the temperature. The absorption spectra of FIG. 2 for the main constituents of alcohol-containing probes, water and alcohol, in the wave length range between 1100 nm and 1300 nm, and particularly from 1150 nm to 1250 nm, show that the absorption coefficient of ethanol has a pronounced peak or maximum. In the same wave length range, the absorption coefficient of water is essentially constant or, at a minimum, has a linear absorption characteristic. It can further be seen that the absorption coefficient for ethanol is above that for water in the wave length range of 1170 nm to 1200 nm, which is more clearly seen in the diagram of FIG. 3. FIG. 3 clearly shows that in the mentioned wave length range the absorption coefficient of water is nearly constant.

In addition to the absorption spectra for water and ethanol, FIG. 3 shows for the illustrated wave length range the absorption coefficient for fructose, glycerin and maleic acid, which are common byproducts of wine. FIG. 3 further shows that in the preferred wave length range from 1170 nm to 1200 nm in addition to the characteristic behavior of the absorption coefficients for ethanol and water, the absorption coefficients for the most important other substances behave essentially linearly and are partially offsetting. This makes it possible, for example, to determine the value $\Delta A$ representative of the relationship of the measured absorption values, particularly when using several wave lengths for both the calibration measurements and the absorption measurements on the probe under investigation. In this manner, the absorption proportions of the other substances can readily be taken into consideration, or they cancel each other out.

The determination of alcohol concentrations in probes with different alcohol content or differing constituents is further described by reference to the following examples:

EXAMPLE 1

Alcohol determination of wine:
Used wave lengths: 1178 nm, 1183 nm, 1190 nm
Measured absorptions: $A_{1178}$, $A_{1183}$, $A_{1190}$
A value $\Delta A$ is determined as follows:

$$\Delta A = A_{1183} - (7/12 * A_{1178} + 5/12 * A_{1190})$$

This value $\Delta A$ is a function of the alcohol concentration (k):

$$\Delta A = a*k + b$$

wherein a and b are calibration constants from an earlier measurement with a probe of known concentration, and for wine they amount to approximately $a = 1 \cdot 10^{-3}$ and $b = 1 \cdot 10^{-4}$.

Attained accuracy $\pm 0.1\%$ by volume.

It is immediately apparent that the alcohol concentration of the probe under investigation is directly determined with a simple approximation method. The simple constants needed for determining the value $\Delta A$ are obtained from the essentially linear behavior of the absorption coefficients for the added substances, and they can be determined with simple calibration measurements. It should further be noted that the calibration constants needed for determining the value $\Delta A$ can uniformly be used for wines over a large concentration range because the possibly differing proportions, especially of added substances, are sufficiently taken into consideration due to the linear absorption characteristic of the correction values.

EXAMPLE 2

Alcohol measurement of beer:
Used wave length: 1178 nm, 1183 nm, 1188 nm
Measured absorptions: $A_{1178}$, $A_{1183}$, $A_{1188}$
The value $\Delta A$ is determined as follows:

$$\Delta A = A_{1183} - (\tfrac{1}{2} * A_{1178} + \tfrac{1}{2} * A_{1188})$$

the value $\Delta A$ is again a function of the alcohol concentration (k):

$$\Delta A = a*k + b$$

wherein a and b are calibration constants and are approximately $a = a \cdot 10^{-4}$ and $b = 1 \cdot 10^{-4}$.

Attained accuracy ±0.1% by volume.

EXAMPLE 3

Alcohol measurement of beverages with high alcohol content (brandies):
Use wave lengths: 1178 nm, 1184 nm, 1188 nm
Measured absorptions: $A_{1178}$, $A_{1184}$, $A_{1188}$
The value $\Delta A$ is determined as follows:

$$\Delta A = A_{1184} - (0.6 * A_{1178} + 0.4 * A_{1188})$$

This value $\Delta A$ is again a linear function of the alcohol concentration (k):

$$\Delta A = a*k + b$$

wherein a and b are calibration constants and are approximately $a = 9 \cdot 10^{-4}$ and $b = a \cdot 10^{-4}$ for brandies.

Effective range: 25% by volume to 50% by volume

Attained accuracy ±0.1% by volume.

With respect to examples 2 and 3, it is to be noted that analogous to the illustration of added substances for wine in FIG. 3, a small number of added substances can generally be determined for beer and high alcohol content beverages. They too have an essentially linear characteristic in the indicated wave length range. Thus, a precise and exact determination of the alcohol content can be made with the help of simple correction values or calibration constants. A simple determination of the alcohol concentration over a wide concentration range becomes thereby possible.

The alcohol content of healing preparations, for example, as well as alcohol-containing cosmetic products, can be determined in a manner analogous to the above-described examples by taking into consideration the substances that are present in the products in addition to water and alcohol.

What is claimed is:

1. A method for spectroscopically determining a concentration of alcohol in a liquid probe, comprising:

measuring absorption of light by a calibration probe having a known concentration of alcohol, thereby generating calibration data;

measuring absorption of light by the liquid probe at one or more wavelengths, including at least a first wavelength that is between 1100 nm and 1250 nm and at which an absorption coefficient of an alcohol exceeds an absorption coefficient of water, thereby generating test data; and computing the concentration of alcohol in the liquid probe directly from the test data and the calibration data.

2. The method according to claim 1, wherein the first wavelength is between 1170 nm and 1200 nm.

3. The method according to claim 1, wherein the first wavelength is in a wavelength range within which an absorption coefficient for a substance in the probe other than alcohol varies substantially linearly with wavelength.

4. The method according to claim 1, wherein the first wavelength is in a wavelength range within which an absorption coefficient for water varies substantially linearly with wavelength.

5. The method according to claim 1, wherein the one or more wavelengths further include a second wavelength between 1100 nm and 1250 nm.

6. The method according to claim 5, wherein the concentration of alcohols is computed from the absorption data and the calibration data using a linear approximation method.

7. The method according to claim 1, wherein the alcohol concentration of the liquid probe is less than 60%.

8. The method according to claim 1, further comprising:

during measuring absorption of light by the liquid probe, maintaining a temperature of the liquid probe at a substantially constant value.

9. The method according to claim 8, wherein the substantially constant value is constant to within 0.2° C.

10. The method according to claim 1, further comprising:

during measuring absorption of light by the liquid probe, measuring a temperature of the liquid probe; and during computing the concentration of alcohol in the liquid probe, accounting for the measured temperature of the liquid probe.

11. A method for spectroscopically determining a concentration of alcohol in a liquid probe, comprising:

measuring absorption of light by the liquid probe at at least one wavelength between 1170 nm and 1200 nm, thereby generating test data; and computing the concentration of alcohol in the liquid probe directly from the test data and a calibration based on the measured absorption.

* * * * *